United States Patent
Stringer

(10) Patent No.: US 6,602,708 B1
(45) Date of Patent: Aug. 5, 2003

(54) NEURAL CULTURES

(75) Inventor: Bradley Michael John Stringer, Cardiff (GB)

(73) Assignee: CellFactors plc, Cambridge (GB)

( * ) Notice: Subject to any disclaimer, the term of this patent is extended or adjusted under 35 U.S.C. 154(b) by 0 days.

(21) Appl. No.: 09/454,446

(22) Filed: Dec. 6, 1999

Related U.S. Application Data

(63) Continuation of application No. 08/836,441, filed on May 8, 1997, now abandoned.

(30) Foreign Application Priority Data

Nov. 8, 1994 (GB) .............................................. 9422643

(51) Int. Cl.⁷ .............................. C12N 5/08; C12N 5/10
(52) U.S. Cl. ...................... 435/368; 435/325; 435/373; 435/377; 435/384; 435/391
(58) Field of Search ..................... 514/12, 44; 435/325, 435/368, 373, 377, 384, 391

(56) References Cited

U.S. PATENT DOCUMENTS 5,580,777 A * 12/1996 Bernard et al.
5,672,499 A * 9/1997 Anderson et al.

OTHER PUBLICATIONS

Onife et al. *Cell Transplantation*, vol. 6, pp. 327–338, 1997.*
Eves et al. *Brain Research*, vol. 656, pp. 396–404, 1994.*
Stringer et al., *Dev. Brain Res.*, vol. 79, pp. 267–274, 1994.*

* cited by examiner

*Primary Examiner*—Gary Kunz
*Assistant Examiner*—Stephen Gucker
(74) *Attorney, Agent, or Firm*—Klauber & Jackson

(57) ABSTRACT

Production of fully differentiated, optionally immortalized, neural cells—by enhancing replication then inducing differentiation by mimicking cell's natural environment in vitro. The cells are useful for transplantation or drug screening.

10 Claims, 4 Drawing Sheets

Figure 1:
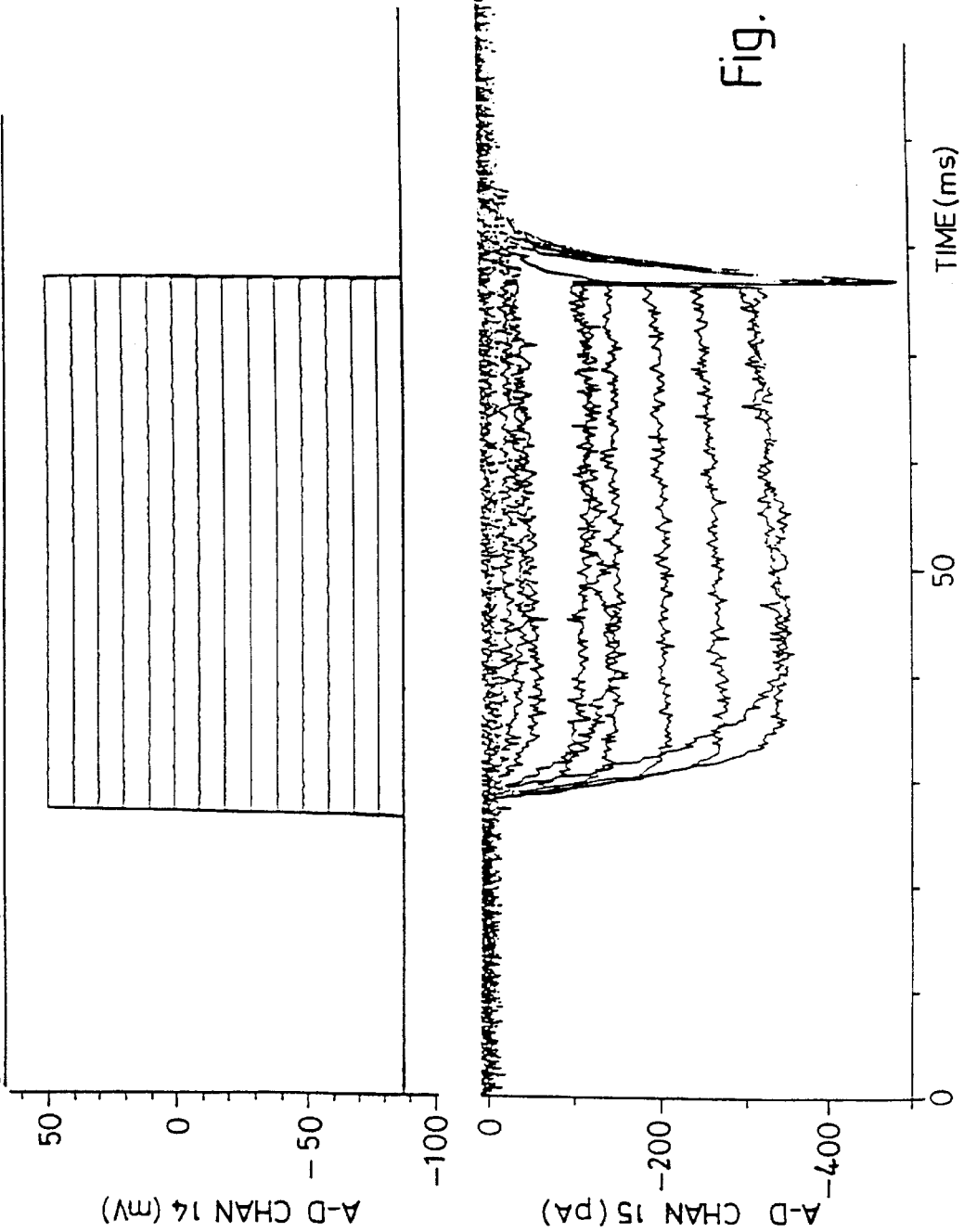

Summary of experiments performed with Clone1 immortal cell line

| Cell | ICa (5mM Ca) | IBa (30mM Ba) | ω-CgTxGVIA | ω-AgaIVA |
|---|---|---|---|---|
| 1 (2week) | 0 | nd | nd | nd |
| 2 (2week) | <50pA | nd | nd | nd |
| 3 (2week) | 0 | nd | nd | nd |
| 4 (2week) | 0 | nd | nd | nd |
| 5 (2week) | 0 | nd | nd | nd |
| 6 (2week) | 0 | nd | nd | nd |
| 7 (2week) | <50pA | nd | nd | nd |
| 8 (2week) | >100pA | >200pA | 100% @1µM | nd |
| 9 (2week) | >100pA | >200pA | 70% @100nM | insensitive (50nM) |
| 10 (4week) | 0 | 0 | nd | nd |
| 11 (4week) | nd | <50pA | nd | nd |
| 12 (4week) | 0 | >200pA | 70% @1µM | nd |

6/12 cells had ICa
Predominantly N type
In one cell, residual current not inhibited by ω-AgaIVA Table 1

NEURAL CULTURES

This application is a continuation of application Ser. No. 08/836,441, filed May 8, 1997, now abandoned.

The invention relates to a method of producing neural cultures and particularly, but not exclusively, neural cell-lines; and the cells and cell-lines produced by such a method.

The invention also relates to human and animal neural cell-lines, and particularly but not exclusively, nerve cell-lines.

Nerve cells are highly differentiated cells comprising a cell body, and processes, the latter subdivided into dendrites and axons. Nerve cells vary considerably in shape and size in different parts of the body. For example, granule cells from the cerebellum are 5 micrometres in diameter whereas the large motor cells of the anterior horn of the spinal cord are up to a 120 micrometres in diameter. In addition, the axons of nerve cells vary from about a hundred micrometres in length up to 1 metre in length. In addition to this variation in shape and size nerve cells also vary in the nature of the receptors expressed on their cell surface and the nature of the neurotransmitters secreted for the purpose of effecting nerve cell transmission. This difference in biochemistry can be used for the purposes of classification. Thus, in simplistic terms, nerve cells may be classified as, for example, adrenergic, cholinergic, serotoninergic, dopaminergic etc according to the nature of their neurotransmitters. This biochemical mode of classification can be further sub divided in order to identify a whole range of nerve cells secreting different neuropeptides that are thought to function as neurotransmitters or neuromodulators such as the neuropeptides beta endorphin, met—enkephalin, somatostatin, luteinizing hormone—releasing hormone, thyrotropin releasing hormone, substance P, neurotensin, angiotensin 1, angiotensin 2, vasoactive intestinal peptide, neuropeptide Y, calcitonin gene related peptide etc, or alternatively, the amines or amino acids, adrenalin, noradrenaline, octopamine, serotonin, histamine, gamma aminobutyric acid, and taurine. The afore list is not intended to be exhaustive but rather serves to illustrate the nature of the biochemical diversity of nerve cells.

It is widely acknowledged that it would be immensely advantageous if it was possible to provide ideally in culture a homogeneous population of nerve cells and so provide, for example, a homogeneous population of nerve cells either from a given location in the central nervous system, or alternatively, a homogeneous population of nerve cells exhibiting either predetermined morphological characteristics and/or biochemical characteristics. For instance it would be highly advantageous if it was possible to provide a homogeneous population of nerve cells which were characterised by either the transmitter secreted in response to activation or alternatively the receptor occupied in response to activation. With such a population of nerve cells it would be possible for research biologists to make significant advances in the understanding of the nervous system and for industrial biologists to manufacture and test drugs, agents or entities which affect the functioning of a given population of nerve cells with a view to developing therapeutically active agents.

In addition, if it was possible to provide a homogeneous population of nerve cells it would be possible to provide nerve cells of a given classification for the purpose of transplantation. This would be particularly appropriate in cases where nerve cell degeneration or damage had occurred. For example, it is well known that Parkinson's Disease is related to nerve cell degeneration and a corresponding lack of secretion of dopamine by nerve cells. Thus, if it was possible to provide a homogeneous population of nerve cells that secrete dopamine then it would be possible to transplant such nerve cells and thus mitigate or alleviate or even reverse the symptoms of Parkinson's Disease. Similarly, other forms of dementia which are characterised by a progressive degeneration of nerve cells could be treated in a similar manner. Similarly, acute destruction of nervous tissue could be treated by nerve cell implants comprising a homogeneous population of nerve cells and/or the implantation of a selected combination of nerve cells from different homogeneous populations.

However, the above referred to diversity of nerve cells and also the postmitotic nature of nerve cells tend to impose severe restrictions on the number of cells that can be obtained in vitro for investigation and/or transplantation using conventional cell culture techniques. For this reason attempts have been made to provide cultures of nerve cells by cultivating primary tumour tissue or by fusing primary cells with tumour cells. However, tumour cells are irreversibly transformed and have an ill-defined history. Their use as cell models is therefore highly questionable and moreover because of the potential tumorigenicity of such tissue they cannot be used for the purpose of transplantation.

Attempts to provide homogeneous populations of nerve cells have also been undertaken using carcinogen-induced transformation both in vivo and in vitro and also by spontaneous transformation that is to say by the out growth of cells from primary cultures without any deliberate genetic manipulations.

However, it has been found that another restriction on the provision of homogeneous populations of nerve cells concerns the fact that most neural tumours are human glioblastomas and thus do not concern the uncontrolled division of functional nerve cells.

Other workers have transfected neural cells with oncogenes in order to establish neural cell-lines. Some workers have shown that it is possible to induce oncogenes into primary neural cells and to obtain cell-lines, however, these cell-lines are not nerve cell-lines. They are not functioning nerve cells nor are they homogeneous populations of definable nerve cells (1).

The transfection techniques used in the past have involved the use of retroviruses because of the ability of such viruses to stably integrate into the host cell genome. In addition, transfection has been undertaken using a temperature sensitive mutant of the DNA virus simian virus 40 (SV40). The A gene of SV40 encodes the large tumour (T) antigen which is required for the initiation and maintenance of transformation.

Integration of viral genes into host cell genomes requires that the host cell undergoes at least one round of DNA synthesis. It therefore follows that where integration of a viral gene into a host cell is required target cells are limited to mitotic neural cells. Transfection techniques have therefore been undertaken on such cells. Although it has been possible to produce cell-lines, that is to say it has been possible to immortalise the transfected cells, it has not been possible to produce immortalised cells with the required degree of differentiation which would render such cells as useful tools for further research, study or use. This would seem to be because immortalisation prevents terminal differentiation of nerve cells. Indeed, typically the cells enter crisis and apoptosis ensues. For example, when immortalisation of neural cells takes places using SV40 T a homogeneous population of cells can be cultured, however at a non permissive temperature of 39° C. expression of the active viral protein ceases and the cells enter differentiation. However, differentiation does not proceed to completion, the cells enter crisis and apoptosis ensues.

In addition, it also widely acknowledged that it is extremely difficult to provide in culture differentiated neural or nerve cells either for use in transplantation and/or for use in testing drugs, agents or entities which effect the functioning of a given population of nerve cells with a view to developing therapeutically active agents. It is difficult to provide such a culture of nerve cells, especially where one is trying to provide, largely, a homogeneous population of nerve cells, or a heterogeneous population of nerve cells including a relatively small number of phenotypes, because, amongst other things, it is very difficult to provide for differentiation of such nerve cells. Typically it is difficult to provide for differentiation of primary nerve cells in culture.

It is therefore an object of the invention to provide a method for producing nerve cell-lines which represent homogeneous populations of nerve cells which are not only functional but whose character can be reliably defined. In other words it is an object of the invention to provide a method for producing a stable nerve cell-line which is committed to its phenotype. For example, using the invention it is possible to provide a homogeneous population of functional serotonin cells or acetylcholine cells or adrenalin cells etc.

It is a further object of the invention to provide a non-mitotic cell-line, whose non-mitotic characteristics persist even in the presence of factors and/or conditions which would normally promote mitosis.

It is yet a further object of the invention to provide a cell-line which survives at low densities.

It is also an object of the invention to provide a method for producing nerve cell-lines which can be selectively made to enter apoptosis so that the process of apoptosis can be studied with a view to gaining a greater understanding of the process and also with a view to engineering drugs, agents or entities that affect apoptosis.

It is yet a further object of the invention to provide for a population of nerve cells, homogeneous or otherwise which are fully differentiated.

The method of the invention is based on a startling observation. Using conventional transfection techniques we were able to immortalise selected neuronal cells. However, as with many other workers, until realising the invention, we were unable to provide fully functional differentiated nerve cells. However, when we modified our method for producing cell-lines we found that we were able to induce full differentiation of our nerve cells when they were exposed, following transfection and immortalisation, to predetermined conditions. These conditions involved exposing the cells to either the environment from which they came and particularly, but not exclusively, the mitotic environment from which they came or to conditions which mimicked the environment from which they came and thus provided for an artificial imitation of the environment from which they came.

Our observation has also enabled us to produce an in vitro culture of nerve cells which have not been immortalised. In this instance, primary nerve tissue is first encouraged to replicate by exposure to a replicating agent (8 and 9) and is then encouraged to differentiate by exposing the cell culture to the aforementioned environment from which said primary tissue came or to conditions which mimic said environment.

By the term, the environment from which they came, we mean a region of the central nervous system, and more preferably a region of the central nervous system at, adjacent, or functionally related to the natural location in the central nervous system of the cultured cells. We favour a mitotic environment therefore we favour a region from the central nervous system which is mitotically active and more preferably we favour a region from the central nervous system at, adjacent, or functionally related to the natural location in the central nervous systems of the cultured cells.

It would seem that having to expose the cells to the environment from which they were derived means that cells of that environment secrete agents, such as for example cytokines, growth factors, transmitters etc or perhaps such cells comprise removable cell surface based factors, which can elicit a differentiation response.

In addition, we have found that it is possible to use tissue and cells from different species in order to work the invention. For example, it is possible to culture human nerve cells and expose such human nerve cells to said environment or said artificial environment which is derived from rat central nervous system. Conversely, it is possible to culture rat nerve cells and expose said nerve cells to an environment or artificial environment which is human derived.

It would therefore seem that agents which elicit neuronal differentiation of the invention are agents which can elicit their effects cross species. That is to say these agents are biologically active in at least both rat and human systems and are therefore likely to be of the same or similar structure.

Thus we have found that modifying our method such than transfected cells or cultured cells are exposed to the conditions of the original environment at least from which the first culture cell came brings about differentiation. We are unclear as to the nature of the factors involved at this stage.

Further, when using transfected cells we prefer to employ a method which includes the provision of a switch which enables us to control immortalisation and apoptosis. Using our method we have found that cultured nerve cells do not spontaneously undergo apoptosis so frustratingly characteristic of previously cultured neural cell-lines, but rather we can selectively control whether cell-lines remain immortalised or enter apoptosis.

In addition, we have also found that our cell-lines when differentiated, are committed to their phenotype and thus retain their phenotypic characteristics even when the environment from which they came is removed and/or they are exposed to factors such as foetal calf serum. Further, we have also found that our cell-lines do not exhibit mitosis, again, even under conditions which would promote mitosis, and, what is more, our cell-lines are able to survive at low densities.

According to a first aspect of the invention there is therefore provided a method for producing large populations of neural cells which method involves:

a) enhancing the replication of a first undifferentiated neural cell, or neural cell precursor cell, or precursor stem cell, b) exposing said replicated neural cells either to an environment from which said first neural cell came, or to an environment which mimics said environment; and c) allowing differentiation of said cells to produce fully differentiated active neural cells.

It is apparent from the above that using the method of the invention one is able to culture and/or immortalise a neural cell precursor cell and thus produce a homogeneous population of cells. However, successful differentiation is effected by exposing the cells to either the environment from which the first nerve cell came or alternatively to an environment which mimics that environment. In this way, it is possible to produce a homogeneous population of fully differentiated active neural cells.

In a first embodiment of the invention the environment from which the first nerve cell came is any region of the central nervous system, however, more preferably, said environment is an environment at, adjacent, or functionally related to the natural location in the central nervous system from which the cultured cells derive. The term, an environment which mimics said environment, is also to be construed accordingly.

More preferably still, said environment is a mitotic environment, that is to say, it comprises cells undergoing mitosis. It would seem that in this instance the agent(s) which elicit the differentiation process are being released or expressed and somehow affecting differentiation by cells within the mitotic cells environment.

Preferably, said nerve cells and tissue from said natural or artificial environment is derived from a single species. However, alternatively, said nerve cells and said tissue may be derived from different species. For example, said nerve cells may be derived from foetal human tissue whereas said environment and more specifically said tissue of said environment may be derived from an another animal species such as rat, mice, monkeys etc.

In a preferred embodiment of the invention immortalisation is achieved by using conventional transfection techniques and preferably the transfection involves the incorporation into the cell genome of an oncogene which oncogene favours the establishment of cell division well beyond the normal level encountered when a cell is not transduced with an oncogene, in other words the oncogene immortalises the cell.

Alternatively, immortalisation may be effected using physical or chemical means. For example, immortalisation may be effected by exposing said cell to radiation or chemicals (2) which are known to promote cell division well beyond the normal level encountered when a cell is not exposed to said physical and chemical means.

Ideally transfection is undertaken using a virally derived oncogene such as a myc, src, ras, SV40T, or a retroviral construct including any of the aforementioned oncogenes and/or any human oncogenes. A retroviral construct is favoured because of its ability to stably integrate into the host cell genome.

In a first preferred embodiment of the invention the immortalising agent includes or has associated therewith a control means whereby activation of the control means terminates immortalisation and causes the cell to enter apoptosis.

It is preferred that immortalisation of said cell with an immortalising agent takes place ideally during the last division before migration from the proliferative zone and the onset of terminal differentiation. This is because the likelihood of producing a cell-line having a single set of functional characteristics is increased. Immortalisation prior to this preferred time can be undertaken but the likelihood of the precursor cells adopting several different phenotypes after differentiation is increased.

In a preferred embodiment of the invention the control means is responsive to culture or environmental conditions such as temperature, pH or ionic concentrations. For example, in a preferred embodiment the immortalising agent is temperature sensitive and the control is thus represented by a temperature sensitive switch so that at, about, or below a first given temperature the immortalisation agent is activated so as to immortalise the selected nerve type, but at, about, or above a second temperature the immortalising agent is deactivated and in this instance immortalisation terminates and apoptosis is allowed to proceed. The immortalisation agent and the control means may comprise, for example, a single entity such as a temperature sensitive oncogene. Alternatively, the immortalisation agent and the control means may be two independent entities but in either case ideally the activation/deactivation of the control means has a reciprocal effect on the immortalisation agent. For example, when the control means is activated the immortalisation agent is deactivated. Conversely when the control means is deactivated the immortalisation agent is activated. This ability of the control means to deactivate the immortalisation agent is a means of terminating immortalisation such that apoptosis can take place.

Exposing said cells to the original environment can involve transplanting said homogeneous population of cells back into the central nervous system or more preferably a location in the central nervous system at, adjacent or functionally related to the original environment of the first cell or alternatively, and more preferably, simply extracting a population of cells from said central nervous system or said original environment and placing said extracted population in close proximity to said homogeneous population of cells.

Ideally, said chosen environment comprises mitotically active cells.

In the instance where said cell is exposed to an extracted population of cells then ideally said extracted cells are plated onto a substrate and allowed to reach confluence either before being placed in contact with said homogeneous population of cells or whilst in contact with said homogeneous population of cells. Alternatively, said extracted population of cells are grown to confluence and medium from said population is added to said homogeneous population of cells in order to bring about differentiation.

Preferably, said homogeneous population of cells are also exposed to one or more growth factors such as fibroblast growth factor and/or epidermal growth factor.

It will be apparent from the above that the nature of the homogeneous population of cells will be determined by the nature of the undifferentiated nerve cell or nerve cell precursor cell. Thus using the method of the invention it will be possible to produce cell-lines of different nerve cells whose function and properties will be determined by the nature of the undifferentiated nerve cells or nerve cell precursor cells. Thus the invention has wide ranging application in that the invention provides a method whereby a whole range of homogeneous populations of nerve cells can be grown in culture. This is obviously significant for neurobiologists both from a research point of view and from a technical point of view.

Preferably the immortalising agent is, what is typically referred to as, a soft oncogene such as a SV40 viral oncogene and more preferably, in the instance where a control means is preferred the oncogene is the SV40 T antigen which is permissive, that is to say the viral gene active product is expressed, at 33° C. and non-permissive, that is to say the viral gene active product is not expressed, at 39° C., thus cells immortalised using this agent are temperature sensitive for apoptosis.

Uniquely, our cells, when transformed using SV40 T antigen and exposed to an environment, natural or artificial, which promotes differentiation, survived crisis—a condition which is typically followed by apoptosis.

It would seem that the said environment also provides for the release of substances or somehow effects the cells to enable them to survive apoptosis.

In yet a further preferred embodiment of the invention said cell-line includes a safety feature which allows for selective disabling or destruction of said cell-line. This safety feature is of advantage where the cell-line is to be used for the purpose of transplantation or is otherwise, whether it be permanent or temporary, attached to, administered to, or stored in, an individual. This safety feature allows the cell-line to be selectively disabled, and by this we mean rendered harmless, or destroyed, in instances where the cell-line is thought likely to, or is shown to, have the potential to become tumorigenic in vivo, or is thought to be in any way harmful to an individual.

Our copending patent application GB 9422236.1 teaches how a vector can be produced which provides for co-expression of a safety feature in the form of a gene which may or may not be linked to the immortalising oncogene.

According to a further aspect of the invention there is provided cells and/or cell-lines produced in accordance with the method of the invention. Accordingly there is provided at least one homogeneous population of immortalised cells which can be made to fully differentiate so as to provide a homogeneous population of fully differentiated nerve cells; and/or alternatively, there is provided at least one homogeneous population of immortalised cells provided with means to terminate immortalisation and activate apoptosis.

According to a yet further aspect of the invention there is provided cells and/or cell-lines produced in accordance with a method of the invention which, when differentiated, retain their phenotypic characteristics and/or are non-mitotic and/or survive at low densities.

An embodiment of the invention will now be described by way of example only and for the purpose of example only with specific reference to serotonin secreting functional nerve cells.

A BRIEF DESCRIPTION OF THE DRAWINGS

Figure 2:
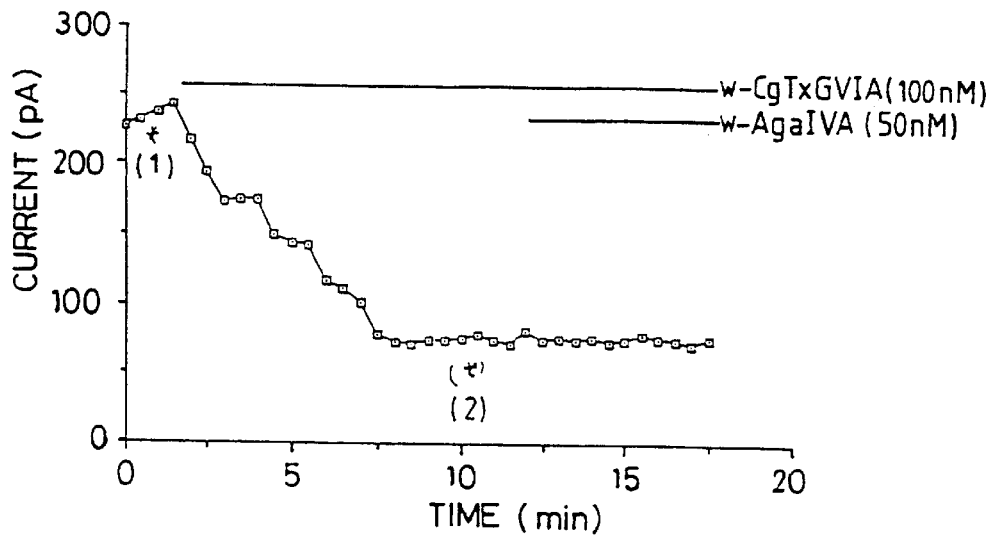
Figure 2:
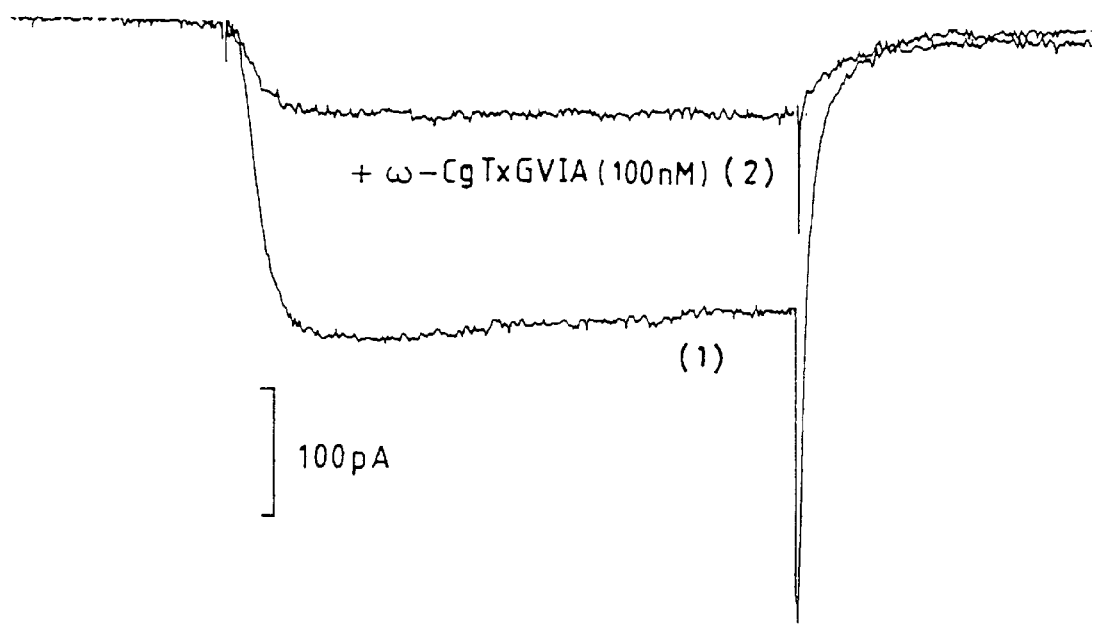
Figure 3:
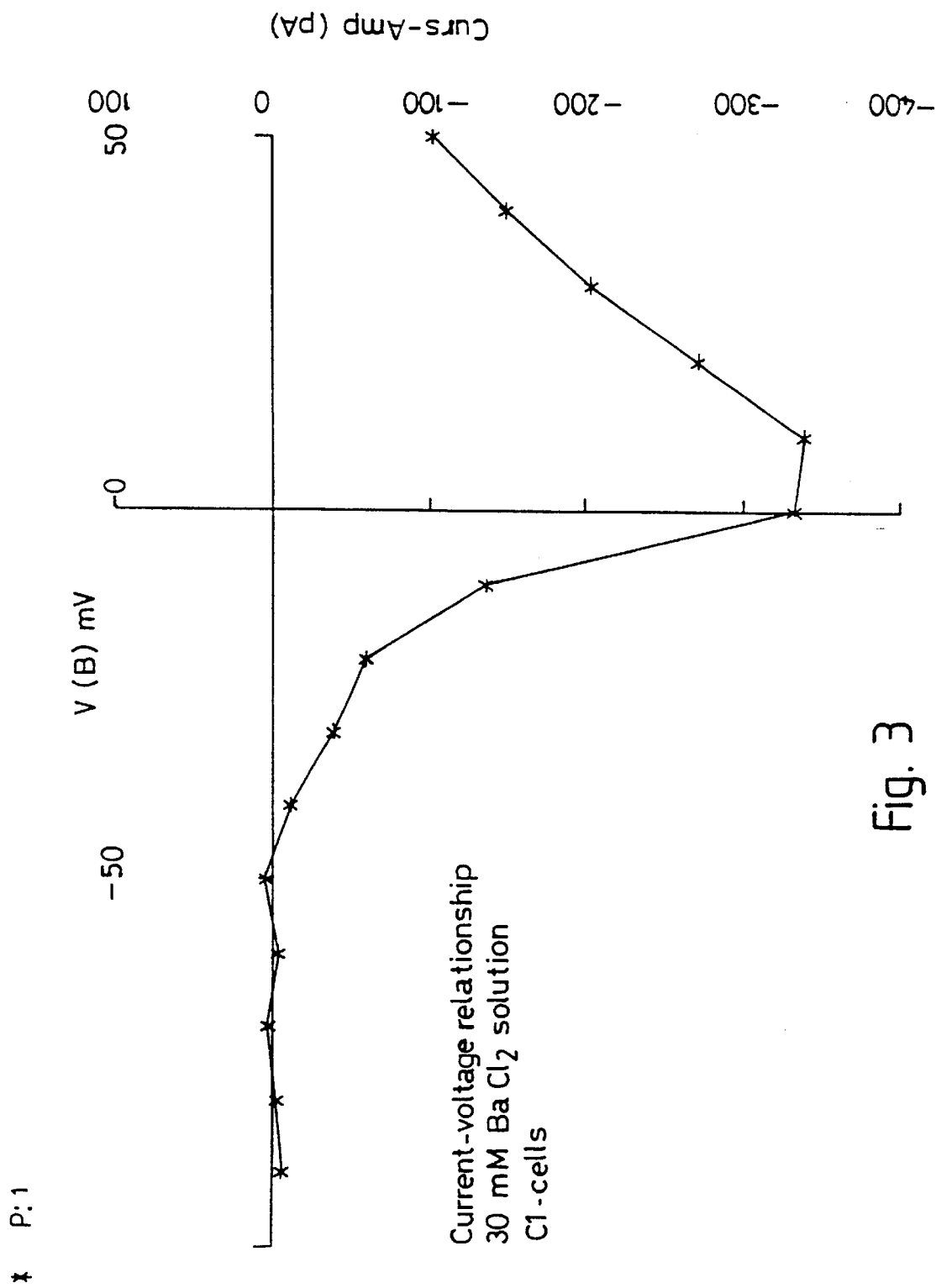

The following is exemplified by a table and a number of figures wherein;
1. Table 1 is a summary of experiments performed with clone 1 immortal nerve cell line.
2. FIG. 1 shows the current—voltage relationship at 30 mM Ba of clone 1 cells one to two weeks after differentiation.
3. FIG. 2 shows time course of VDCC effects of toxin application on clone 1 nerve cells; and
4. FIG. 3 shows current—voltage relationship for clone 1 cells.

IMMORTALISATION OF CELLS

Rat embryos at days 12–13 of gestation were dissected, and the presumptive raphe nuclei region comprising the ventral medial rhombencephalon and medulla oblongata were removed. After dissociation by gentle trituration in medium (Ham's F12/Dulbecco's modified Eagle's medium (50/50 v/v) supplemented with L-glutamine (2 mM), penicillin:streptomycin (100 IU/ml:10 $\mu$g/ml) and modified stock solution [3,4] containing 5 ng/ml basic fibroblast growth factor [5] (all supplied by Sigma), cells were plated onto poly-L-lysine/gelatin-coated 162 cm$^2$ tissue culture flasks (Costar UK Ltd) at a density of 5×10 cells/ml, 20 ml per flask. Once the cells had adhered, retroviral particles comprising a construct (tsA58) incorporating a temperature sensitive form of the simian virus large-tumour antigen (ts)SV40-T and a resistance marker to geneticin, G418' (kindly donated by Dr P Jat, Ludwig Institute, Middlesex Hospital, London. Also available on deposit, details to be provided) [6], were added to the medium together with 0.8 $\mu$g/ml polybrene. The viral titre was adjusted to give a low transduction efficient of 0.0002%, producing an average of 20 colonies per flask. After 1 h, the culture medium was replaced with fresh medium. Cultures were maintained at 33° C., the permissive temperature for the active form of the SV40-T oncogene product. Five days after transduction, geneticin was added to the culture medium (0.4 mg/ml) for a further 8 days to eradicate cells which had not incorporated the retroviral vector.

Between 14 and 20 days after transduction, individual colonies of replicating cells were identifiable. Clones were selected on the basis of being well separated from other replicating colonies, their circular shape and their morphology. Individual clones were picked and expanded up to near confluence in a 75 cm$^2$ flask, ie approximately 23 divisions of a single precursor, prior to freezing down of cell aliquots. Aliquots were also plated onto poly-L-lysine/gelatin-coated 12-well plates for analysis of potential differentiation characteristics.

Alternatively, rat embryos, as aforementioned, were treated so as to provide cells in tissue culture and these cells were then exposed to a replicative agent as described in references 8 and 9 prior to undergoing differentiation as described below.

Cell Differentiation

Cells were maintained in the medium constituents as for replication above and at the permissive temperature of 33° C., but the homogeneous population of nerve cells, now referred to as RAPHE CLONE 1 CELLS, were co-cultured in the bottom of a well with primary RAPHE CELLS (prepared as above but without the steps subsequent to transfection) as a non-confluent cell layer plated on PTFE inserts (Coming). Both the immortalised and the primary RAPHE cells replicated until the primary RAPHE cells became confluent. At this point the immortalised cells exhibited a much reduced replication rate. The primary RAPHE cells were removed by removing the insert and the immortalised cells began to exhibit a significant degree of differentiation. For example, 5-hydroxytryptamine was now synthesized without the requirement for precursor loading, that is native 5-hydroxytryptamine was now demonstrable. Morphological differentiation was much more complex, in that many tapering dendrites, branching often were visualised. In addition, the cells developed several ion channels, including in particular N-type calcium channels. Little or nor apoptosis was seen at the permissive temperature, and the cells were refractory to the glial differentiation-inducing effects of serum.

Cell Apoptosis

The above referred to homogeneous population of raphe clone 1 cells can be caused to enter apoptosis using any of the following four methods.
1. Temperature was raised to non-permissive value (39° C.) for up to 72 h, in the presence or absence of fibroblast growth factor or epidermal growth factor. Neural cells developed the ability to take up 5-hydroxytryptophan (5HTP, the precursor of 5HT), 5HT itself, and to decarboxylate 5-hydroxytryptophan to 5HT. No native 5HT was detectable. The 5HT derived from 5HTP was released, although the mechanism of such release is not known. Weak neurofilament and neurone-specific enolase-like immunoreactivity was demonstrable. Morphological differentiation was limited to development of three or four single-branching neurites. The cells also appeared to undergo extensive apoptosis, such that after three days fewer than 10% remain. The remaining cells were probably neuronal.

2. Temperature was raised to non-permissive value (39° C.) for up to 72 h, in the presence of cyclic AMP plus fibroblast growth factor. Although the parameters of differentiation described above are basically similar after incubation of the cells wish cyclic AMP, there was an increase in the extent of fibre development. The cells were probably neuronal.

3. Temperature was raised to non-permissive value (39° C.) for up to 96 h, in the presence of retinoic acid (10 μM) plus fibroblast growth factor. Cell survival was greatly enhanced, but cells failed to develop the 5HT parameters described above. In addition, neurone-specific enolase staining was much reduced, while conversely glial fibrillary acidic protein immunoreactivity was now found in many but not all the cells. They had taken on a flattened morphology, and no longer exhibited fibrous extensions. The cells were probably glial.

4. Temperature was raised to non-permissive value (39° C.) for up to 96 h, in the presence of 5% foetal bovine serum plus 5% heat-inactivated horse serum plus fibroblast growth factor. Cell survival was greater even than after retinoic acid, and the cells lost the 5HT parameters described above. In addition, neurone-specific enolase staining was dramatically reduced while glial fibrillary acidic protein immunoreactivity was now found in many more cells. The cells took on a flattened morphology, and no longer exhibited fibrous extensions. The cells were probably glial.

We believe that the cells can be made to undergo apoptosis when they reach confluence.

Differentiation Conditions

Mesencephalic and medullary raphe neural cells from the E12–E13 rat embryo (E1=day of conception) were immortalised using a temperature-sensitive oncogene as described earlier (Stringer et al., 1994). Under permissive conditions, ie in the presence of 5 ng/ml of fibroblast growth factor (FGF)(Sigma, product no. F3391) and at 33° C., the immortalised raphe precursor cells replicate. In one clone (921203-6), which possessed all of the characteristics of the clone 921202-6 described in Stringer et al, (1994), shifting the temperature to 39° C., but maintaining all other conditions as before, caused the precursors to develop some of the characteristics of serotoninergic (5HT) neurones, such as neurone-specific enolase- (NSE) and neurofilament- (NF) immunoreactivity, a phase-bright morphology with two or three short bifurcating processes, the ability to take up serotonin via a low-affinity carrier ($K_m$=56 μM) and to decarboxylate 5-hydroxytryptophan (5HTP) to serotonin. Tryptophin hydroxylase activity, however, was not demonstrable, and the cells failed to synthesize serotonin from tryptophan. No calcium channels were demonstrable using patch clamp analysis.

Growing clone 921203-6 raphe precursors tin the presence of primary cells dissected from the same ventromedial regions of the mesencephalon and medulla oblongata from which the clone was originally derived leads to an enhanced differentiation of the clone, provided a mitotic environment is maintained. To establish such conditions, the ventromedial mesencephalon and medulla oblongata were dissected from the E12–E13 rat embryo and plated onto poly-L-lysine coated inserts (PTFE membrane, pore size 0.4 μm, Corning, product no. 25204-6), approximately one mesencephalon/medulla oblongata per insert. The primary cells were incubated under exactly the same replication conditions as those used for obtaining replication in the immortalised precursors ie with 5 ng/ml FGF, and at 33° C. After several days, the density of the primary cells approached confluence. At this time, cells from raphe clone 921203-6 were plated at low density onto a 6-well plate (previously coated with gelatin and poly-L-lysine) and, after confirmation of their attachment to the substrate, the primary cell-containing inserts were placed in the same wells, together with their conditioned medium. No direct contact between primary and clonal cells was possible; diffusible factors in the common medium could have effects on both sets of cells, clonal and primary cells alike, but the effects on the former are undoubtedly direct. Incubation conditions were maintained exactly as before, ie at 33° C., with FGF. After 2–3 days, the immortalised precursors developed a more highly differentiated morphology, with two to three long, tapering and branching processes (presumably dendrites) and a larger phase-bright soma. Immunocytochemical analysis of the clonal cells at this point demonstrated NSE-, NF- and serotonin-immunoreativity, the last even in the absence of loading with 5HT, 5HTP or tryptophan. Calcium channels were now demonstrable, and included presumed N-type, and non-T, non-P type channels also. Once the inserts became confluent, both the primary and the immortalised cells started to exhibit signs of stress and death. Serum failed to prevent this. However, removal of the insert and/or the conditioned medium completely prevented the cell stress and death. Despite the loss of the conditions medium, the immortalised cells continued to display all the parameters described above of the mature 5HT neurones.

Using the mid-line region of the capital E12–E13 rat spinal cord as the source of primary tissue full differentiation of the clonal cells.

Inclusion of foetal calf and heat-inactivated horse serum (both at 5%) in the culture medium had no apparent effect on the differentiated clonal serotonin neurones. By contrast, adding sera to the same cells undergoing the rudimentary differentiation elicited via the temperature-shift method caused them to lose all their neuronal characteristics and adopt instead an astrocytic phenotype.

Counts were made daily of the number of immortalised raphe neural precursors/differentiated serotonin neurones. Although the cells continued to replicate for the first two to three days, as soon as the onset of differentiation became morphologically apparent, replication ceased, even though the cells were still held at 33° C. Removal of the insert after differentiation had been induced led to no increase in cell number; furthermore, no evidence of mitotic bodies was apparent. On the other hand, removal of the insert before differentiation had begun allowed the cells to continue dividing.

In summary, returning immortalised raphe neural precursor cells to the mitotic environment from which they originally came leads to a much more extensive differentiation than previously described methods can provide. The effect is directly on the clonal precursor cells themselves, and is mediated neither via other cell types nor via cell-cell contact. In addition, such differentiation can take place in the presence of a continuing replicative drive, and leads rapidly to a commitment to the chosen phenotype (eg a full-blown serotonin neurone), which is maintained even in the presence of factors which normally cause an alternative phenotype (eg astrocytic) to be expressed. Removal of the conditioning factors does not cause the cells to change from their now committed phenotype. It is likely that soluble factors present in the mitotic primary cell-conditioned medium are responsible for inducing such differentiation, and may be related to the recently described N-terminal cleavage product of sonic hedgehog that is known to induce the differentiation of brainstem and spinal cord precursors to become, respectively, dopaminergic neurones (Hynes et al, Neuron 15(1995)35–44 and cholinergic motoneurones (Roelink et al, Cell(1995)445–455).

Provision of Nerve Cell-lines Including at Least One Selectively Controllable Safety Feature Another preferred embodiment of the invention concerns the preparation of homogeneous populations of cells by retroviral transduction, but also incorporating a safety feature which enables the cells to be selectively disabled and/or destroyed if needs be. This would be seen as advantageous when such cell-lines are used for transplantation into patients to alleviate the symptoms of neurogenerative disorders.

The safety feature would allow the transplant to be selectively destroyed in, for instance, situations where the transplanted material may become tumourigenic in vivo and/or situations where the transplanted material becomes harmful in any other way. Ways in which this could be done are numerous and well known to the man skilled in the art. For example, the cell-line may be transfected with a gene which when activated acts, either directly or indirectly, to bring about disabling or destruction of the transplant. Examples of such genes are well known to those skilled in the art and will not be described herein in greater detail.

In a preferred embodiment of the invention a safety feature may be coupled to the transforming oncogene such that coexpression of the two corresponding cell products occurs. This means that in instances where the oncogene would be activated so too would the safety feature and thus the dangers associated with the tumourigenic nature of the oncogene would be overcome. Coexpression could be achieved in a number of ways for example, the safety gene could be placed downstream of the immortalising gene and next to but 3' to for example a poliovirus derived internal ribosomal entry site sequence (IRES). In this way the same promoter/enhancer(s) controlling the transcription of the immortalising gene would, equally, control the transcription of the safety feature. This is because they would be transcribed as one complete unit, including the IRES sequence which would sit in between them. The IRES sequence allows the translation of sequences downstream of it which code for a separate protein from the sequence 5' of it. The ability to provide such a vector, once given the idea, is well within the range of expertise of a man skilled in the art.

Experiments to Show Functional Characteristics of the Differentiated Nerve Cell-lines Functional Ion Channels Table 1 shows the functional activity of clone 1 immortalised nerve cells under varying neurophysiological conditions.

Twelve different cells were examined either 2 or 4 weeks after differentiation to a fully differentiated nerve cell was complete. Using conventional patch clamp techniques the conductivity of ion channels within the nerve cells examined was determined at either 5 mM Ca or 30 mM Ba. At 5 mM Ca cells 2 and 7 showed a conductivity of less than 50 pA. Cells 8 and 9 showed a conductivity of greater than a 100 pA. These results indicate that clone 1 included functional nerve cells. At 30 mM Ba cells 8 and 9 showed functional ion channels having a conductivity greater than 200 pA. Cells 11 and 12 also showed conductivity under these conditions. A weak signal of less than 50 pA was shown for cell 11 and a stronger signal of greater than 200 pA was shown for cell 12.

Exposure of cells from clone 1 to toxins known to interfere with calcium ion channel conductivity affected the conductivity of clone 1 functional nerve cells. Specifically, at 1 mM w-CgTxGVIA, a toxin known to block N-type calcium channels, cell 8 was 100% affected. As a lower concentration of 100 nM cell 9 was 70% affected. At 1 mM cell 12 was also 70% affected. These results indicate that factors which specifically affect nerve cell conductivity affected the differentiated nerve cells in clone 1 and thus indicate and these differentiated nerve cells were fully functional nerve cells expressing phenotypic characteristics and more specifically nerve cells possessing N-type calcium channels.

Use of the toxin w-Aga IVA, is a toxin known to block P-type calcium channels, was less successful at a concentration of 50 nM cell 9 was insensitive.

Referring now to FIG. 1 current voltage data is available for clone 1 cells. A range of voltages between −85 and 50 mv were applied to the cells of the invention. Simultaneously the response of said cells was monitored by recording current flow. Voltages above resting potential elicited current flow and thus opening of nerve cell ion channels. A depolarising potential was observed at approximately minus 50 mv. This depolarising potential resulted in a generation of an action potential indicating that the cells are fully functional. The cells were inactive at approximately 10 mV.

FIG. 2 shows a time course of voltage dependent channel conduction and the effects of toxin application on this conductivity. Over a period of approximately 5 minutes the application of w-CgTxGVIA resulted in a marked reduction in nerve cell conductivity. After a 10 minute interval a second toxin was added and the current remained at approximately 70 pA. The current voltage relationship is shown towards the bottom of FIG. 2 where it can be seen that the addition w-CgTxGVIA at a concentration of a 100 nM significantly affected the conductivity of the nerve cell ion channels. The addition of w-AgaIVA also affected nerve cell conductivity but much less markedly.

Finally FIG. 3 shows the current voltage relationship at 30 mM Ba $Cl_2$ solution for clone 1 cells. At a depolarising potential of −50 mV nerve cell ion channels are opened and current in the order of −350 pA flows.

We also have data showing that our ells include fully functional voltage dependant potassium channels which are blockable using conventional physiological tools, (data not shown).

The above data indicates that the nerve cell clones of the invention can be made to fully differentiate and thus exhibit phenotypic characteristics of a fully functional and thus fully differentiated nerve cell.

References

1. White L A and Whittemore S R., Immortalisation of Raphe Neurons: an Approach to Neuronal Function in vitro and in vivo, *Journal of Chemical Neuroanatomy*, Vol 5:327–330 (1992).
2. Stampfer M R, Bartley J C 1985. Induction of transformation and continuous cells lines from normal mammary epithelial cells after exposure to benzo[a]pyrene. Proc Natl Acad Sci USA 82:2394–2398.
3. Bottenstein, J E and Sato G H., Growth of a rat neuroblastoma cell-line in serum-free supplemented medium, *Proc. Natl Acad. Sci.*, 76(1979) 514–517.

4. Romijn H J., Mud M T., Habets, A.M.M.C. and Wolters P S., A quantitative electron microscopic study of synapse formation in dissociated fetal cerebral cortex in vitro, *J Neurophysiol.*, 40(1981) 1132–1150.
5. Murphy M, Drago J and Bartlett P F. Fibroblast growth factor directly stimulates the proliferation and differentiation of neural precursor cells in vitro, *J Neurosci Res.*, 25(1990) 463–475.
6. Jat P S. and Sharp P A., Cell-lines established by a temperature-sensitive simian virus 40 large-T-antigen gene are growth restricted at the non-permissive temperature, *Mol. Cell Biol*, 9(1989) 1672–1681.
7. Stringer B. M. J., et al., Raphe neural cell immortalised with a temperature-sensitive oncogene, Developmental Brain Research 79:267–274, 1974.
8. Reynolds B. A. and Weiff S. Generation of neurons and astrocytes from isolated cells of the adult mammalian central nervous system. Sci. 255:1707–1710, 1992.
9. Mayer E., Dunnett F. B., and Fawcett J. W. Mitogenic effect of basic fibroblast growth factor on embryonic mesencephalic domapinergic neurone precursors. Dev Brain Res 72:253–258, 1993.

What is claimed is:

1. A method for producing a homogeneous population of neural cells which method comprises:
   a) enhancing the replication of an undifferentiated first neural cell with an immortalizing oncogene including, or having associated therewith, a control means responsive to temperature; and
   b) exposing said replicated first neural cell of step a) to an environment by an in vitro incubation step which is selected from the group consisting of:
      (i) incubation in the presence of mitotically active primary cells obtained from the same region of the central nervous system from which said first neural cell came; and
      (ii) incubation in the presence of an extract of mitotically active primary cells obtained from the same region of the central nervous system from which said first neural cell came:

said incubation of said neural cell being carried out to produce fully differentiated active neural cells, committed to a single neural phenotype, but maintaining any replicative drive of undifferentiated neural cells by not raising the temperature to a non-permissive temperature of said oncogene control means.

2. A method according to claim 1 wherein said primary cells are removed from said neural cells when said primary cells reach confluence.

3. A method according to claim 1 wherein said replicated neural cells are exposed to a soluble extract from said primary cells.

4. A method according to any preceding claim wherein said primary cells are from the same species as said first neural cell.

5. A method according to claim 1 wherein said environment is from a different species to that of said first cell.

6. A method according to claim 1 wherein said oncogene is SV40T.

7. A method according to claim 1 which further includes transforming said first neural cell with a safety feature gene which is either constitutive or can be selectively activated so as to enable, in either case, selective disabling or destruction of said differentiated cells.

8. A method according to claim 1 wherein replication step a) is carried out in a medium including at least one added growth factor.

9. A method according to claim 1 wherein incubation step b) is carried out in a medium containing at least one added growth factor.

10. A method according to claim 1 wherein differentiation occurs in a medium containing at least one added growth factor.

* * * * *